(12) United States Patent
Strebelle et al.

(10) Patent No.: US 7,612,244 B2
(45) Date of Patent: Nov. 3, 2009

(54) CATALYST AND GAS PHASE METHOD USING SUCH A CATALYST

(75) Inventors: Michel Strebelle, Brussels (BE); Andre Petitjean, Brussels (BE)

(73) Assignee: Solvay (Societe Anonyme), Brussels (BE)

( * ) Notice: Subject to any disclaimer, the term of this patent is extended or adjusted under 35 U.S.C. 154(b) by 380 days.

(21) Appl. No.: 10/579,094

(22) PCT Filed: Nov. 12, 2004

(86) PCT No.: PCT/EP2004/052942

§ 371 (c)(1),
(2), (4) Date: May 12, 2006

(87) PCT Pub. No.: WO2005/046866

PCT Pub. Date: May 26, 2005

(65) Prior Publication Data

US 2007/0142682 A1    Jun. 21, 2007

Related U.S. Application Data

(60) Provisional application No. 60/539,583, filed on Jan. 29, 2004.

(30) Foreign Application Priority Data

Nov. 14, 2003  (FR) .................................. 03 13370

(51) Int. Cl.
*C07C 19/00* (2006.01)
*B01J 23/00* (2006.01)
*B01J 21/00* (2006.01)
*B01J 20/00* (2006.01)

(52) U.S. Cl. .................. 570/244; 502/302; 502/303; 502/304; 502/327; 502/330; 502/331; 502/332; 502/333; 502/334; 502/339; 502/346; 502/351; 502/355; 502/415; 502/439

(58) Field of Classification Search .............. 502/302, 502/303, 304, 327, 330, 331, 332, 333, 334, 502/339, 346, 351, 355, 415, 439; 570/244
See application file for complete search history.

(56) References Cited

U.S. PATENT DOCUMENTS 3,271,324 A * 9/1966 Hirschler, Jr. et al. ....... 502/331

(Continued)

FOREIGN PATENT DOCUMENTS

DE           1 443 703           3/1969

(Continued)

OTHER PUBLICATIONS

U.S. Appl. No. 11/719,652, filed May 18, 2007, Strebelle, et al.

(Continued)

*Primary Examiner*—Cam N Nguyen
(74) *Attorney, Agent, or Firm*—Oblon, Spivak, McClelland, Maier & Neustadt, L.L.P.

(57) ABSTRACT

The invention provides a catalyst containing active elements including copper deposited on alumina containing at least 0.03 g of titanium, expressed in metal form, per kg of alumina and use thereof in gas hase reactions, such as the oxychlorination of ethylene to 1,2-dichloroethane. This catalyst is suitable for maintaining a constant oxygen content in the tail gases and hence in the recycled gases. The invention further pertains to the use of an alumina containing at least 0.03g titanium, expressed in metal form, per Kg of alumina, as catalyst support and as catalyst diluent. In an example a catalyst containing $CuCl_2$, $MgCl_2$, KCl and LiCl deposited on alumina containing 1.13 g of titanium, expressed in metal form, per Kg of alumina was used for the oxychlorination of ethylene to 1,2-dichloroethane in a fluidized bed reactor.

19 Claims, 3 Drawing Sheets

U.S. PATENT DOCUMENTS

Figure 1:
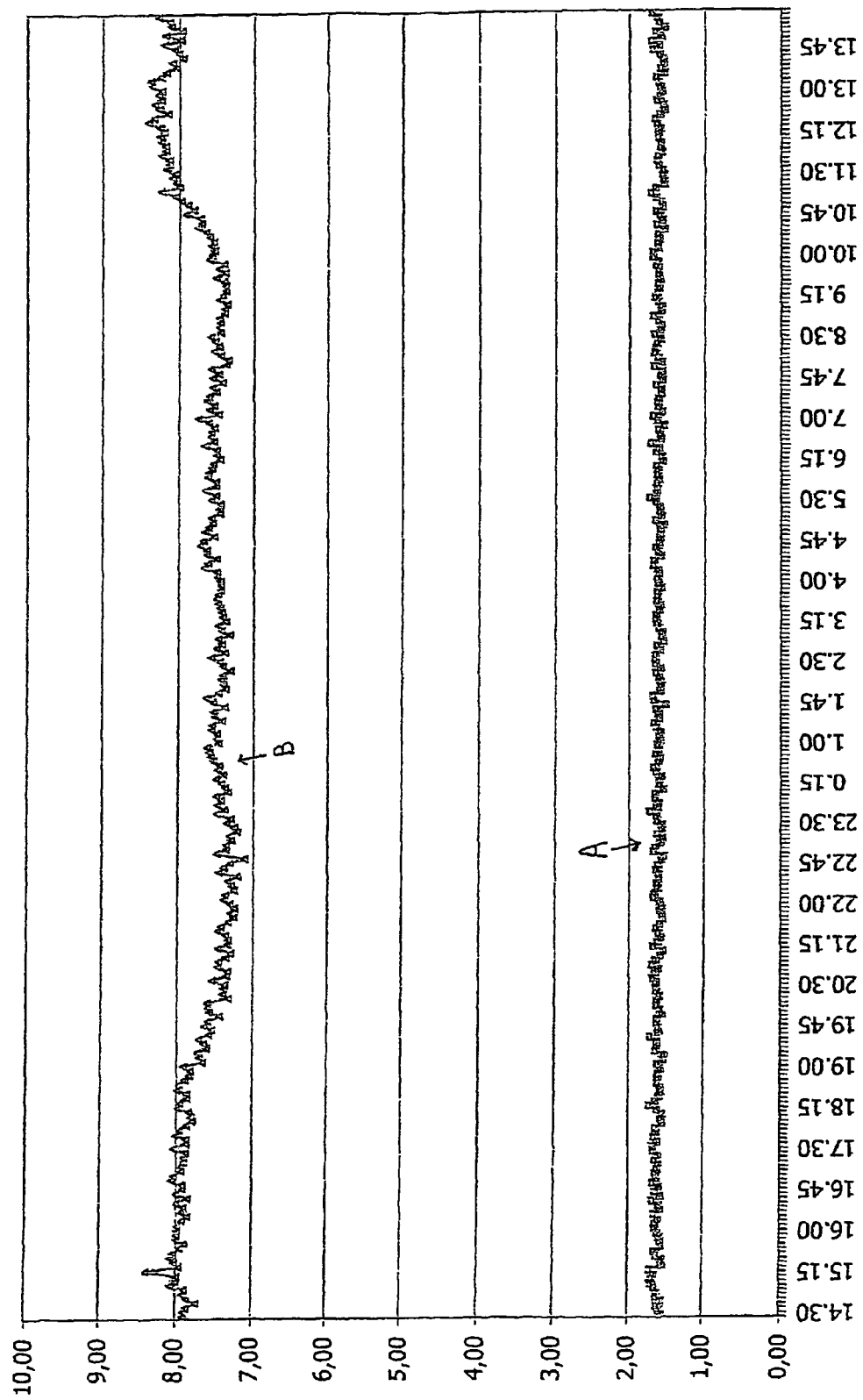

| | | | | |
|---|---|---|---|---|
| 3,397,154 | A * | 8/1968 | Talsma | 502/304 |
| 3,776,854 | A * | 12/1973 | Dautzenger et al. | 252/190 |
| RE27,926 | E * | 2/1974 | Roth | 423/213.2 |
| 4,039,478 | A * | 8/1977 | Cull et al. | 502/242 |
| 4,459,372 | A * | 7/1984 | Arena | 502/351 |
| 4,504,596 | A * | 3/1985 | Schoepe et al. | 502/225 |
| 4,508,848 | A * | 4/1985 | Dolhyj et al. | 502/239 |
| 4,547,487 | A * | 10/1985 | Vogel et al. | 502/351 |
| 5,155,086 | A * | 10/1992 | Thakur et al. | 502/342 |
| 5,478,789 | A * | 12/1995 | Hattori et al. | 502/244 |
| 5,990,040 | A * | 11/1999 | Hu et al. | 502/342 |
| 6,482,766 | B1 * | 11/2002 | Chaumette et al. | 502/242 |
| 6,548,447 | B1 * | 4/2003 | Yokoyama et al. | 502/331 |
| 6,706,660 | B2 * | 3/2004 | Park | 502/304 |
| 7,402,612 | B2 * | 7/2008 | Jin et al. | 518/713 |
| 2002/0007097 | A1 | 1/2002 | Walsdorff et al. | |
| 2002/0131915 | A1 * | 9/2002 | Shore et al. | 422/177 |
| 2002/0147103 | A1 * | 10/2002 | Ruettinger et al. | 502/66 |

FOREIGN PATENT DOCUMENTS

| | | |
|---|---|---|
| EP | 0 255 156 | 2/1988 |
| EP | 0 375 202 | 6/1990 |
| EP | 0 494 474 | 7/1992 |
| EP | 0 657 212 | 6/1995 |
| EP | 0 657 213 | 6/1995 |
| EP | 1 155 740 | 11/2001 |
| FR | 1 360 473 | 5/1964 |
| FR | 1 469 262 | 5/1967 |
| FR | 2 692 169 | 12/1993 |

OTHER PUBLICATIONS

U.S. Appl. No. 11/722,603, filed Jun. 22, 2007, Strebelle, et al.
U.S. Appl. No. 11/722,589, filed Jun. 22, 2007, Balthasart, et al.
U.S. Appl. No. 11/722,598, filed Jun. 22, 2007, Strebelle, et al.
U.S. Appl. No. 11/722,607, filed Jun. 22, 2007, Strebelle, et al.
U.S. Appl. No. 11/914,048, filed Nov. 9, 2007, Strebelle, et al.
U.S. Appl. No. 11/722,587, filed Jun. 22, 2007, Strebelle, et al.
U.S. Appl. No. 11/815,505, filed Aug. 3, 2007, Strebelle, et al.
Anonymous: "Puralox/Catalox—High purity activated aluminas", Internet Article, [online] XP002316203, 2005.

* cited by examiner

CATALYST AND GAS PHASE METHOD USING SUCH A CATALYST

The present application claims the benefit of U.S. provisional application 60/539583 filed Jan. 29, 2004.

The present invention relates to a catalyst and to a gas phase method using such a catalyst.

Gas phase reactions and in particular oxidation reactions generally make use of catalysts comprising active elements deposited on an inert support These supports include alumina, silica gels, mixed oxides and clays or other supports of natural origin.

In the particular case of oxychlorination reactions of hydrocarbons and particularly of ethylene, using hydrogen chloride and air, or oxygen, catalysts consisting of active elements including copper deposited on an inert support like alumina have been very successful.

Thus, patent applications EP-A 255 156, EP-A-375 202, EP-A 494 474, EP-A-657 212 and EP-A 657 213, EP-A 1 155 740 describe catalysts for the oxychlorination of ethylene comprising active elements including copper deposited on an alumina.

In the ethylene oxychlorination methods using air or oxygen, it is customary to recycle the tail gases, after collecting the 1,2-dichloroethane formed and removing the water and all or part of the unconverted hydrogen chloride to upgrade the unconverted ethylene, and thereby to avoid the treatment or venting to atmosphere of large quantities of gas.

Insofar as a combustible gas is recycled via a compressor, the oxygen content of this gas plays a key role in maintaining the safety of the system. Depending on the pressures and temperatures encountered, various oxygen content limitations are imposed. This is why operation with a stable oxygen profile in the tail gases is an important industrial advantage from the standpoint of safety and control of an industrial reactor, and why this advantage is highly prized.

Thus, a catalyst has now surprisingly been found, that is suitable for maintaining a constant oxygen content in the tail gases and hence in the recycled gases.

For this purpose, the present invention relates to a catalyst containing active elements including copper deposited on an alumina, said alumina containing at least 0.03 g of titanium, expressed in metal form, per kg of alumina.

For the purposes of the present invention, alumina means a compound with the formula $Al_2O_3$ such as can result from the calcination of an aluminium hydrate which can, for example, be represented by the formula $AlO(OH).H_2O$ and is characterized by a non-zero specific surface area, advantageously between 50 and 300 $m^2/g$.

The alumina of the catalyst according to the invention contains at least 0.03 g, preferably at least 0.05 g, in a particularly preferred manner at least 0.1 g and in a very particularly preferred manner at least 0.2 g of titanium, expressed in metal form, per kg of alumina.

The alumina of the catalyst according to the invention advantageously contains at most 15 g, preferably at most 5 g and in a particularly preferred manner at most 1.5 g of titanium, expressed in metal form, per kg of alumina The titanium content of the alumina can be measured by any appropriate technique. The titanium content of the alumina is preferably measured by inductively coupled plasma optic emission spectrometry (ICP-OES) after complete dissolution of the sample.

The alumina may be of any origin and may be obtained by any known method inasmuch as it satisfies the titanium contents mentioned above; the titanium having been advantageously introduced into an alumina precursor at a stage prior to the formation thereof, for example in one of the steps of the aluminium hydrate production. The alumina may be entirely or party of type η, γ, θ or δ. It is preferably of type δ or γ and particularly preferably of type δ.

The alumina of the catalyst according to the invention further advantageously has a mean particle diameter between 5 and 200 μm, preferably between 20 and 120 μm The mean particle diameter is preferably established by classifications measured on dry vibrating screens.

The specific surface area of the alumina measured by the BET method with nitrogen is advantageously between 50 $m^2/g$ and 300 $m^2/g$, preferably between 75 and 250 $m^2/g$ and in a particularly preferred manner between 100 $m^2/g$ and 210 $m^2/g$.

The pore volume of the alumina of the catalyst according to the invention is advantageously between 0.1 and 1 $cm^3/g$, preferably between 0.2 and 0.8 $cm^3/g$ and in a particularly preferred manner between 0.25 and 0.6 $cm^3/g$.

Finally, the bulk density (measured by free flow) of the alumina of the catalyst according to the invention advantageously varies between 0.5 and 1 $kg/dm^3$, preferably between 0.6 and 0.9 $kg/dm^3$ and in a particularly preferred manner between 0.65 and 0.75 $kg/dm^3$.

It should be noted that the alumina of the catalyst according to the invention may further contain a variable quantity of atoms other than titanium, such as atoms of alkali metals, silicon or iron that may have been introduced in one of the steps of the aluminium hydrate production.

In the catalyst according to the invention, the active elements are advantageously at least two in number of which one is copper. The catalyst according to the invention therefore contains, in addition to copper, at least one other active element preferably selected from alkali metals, alkaline-earth metals, rare earth metals and metals of the group consisting of ruthenium, rhodium, palladium, osmium, iridium, platinum and gold.

The active elements of the catalyst according to the invention are advantageously present in the catalyst in the form of salts, preferably in the form of chlorides.

Alkali metals means the elements of Group Ia of the Periodic Table. The preferred alkali metals include potassium, sodium, lithium and calcium.

Alkaline-earth metals means the elements of Group IIa of the Periodic Table. The preferred alkaline-earth metals include magnesium, calcium, barium and strontium. Magnesium is particularly preferred.

Rare earth metals means the elements 57 to 71 of the Periodic Table and mixtures thereof.

In the catalyst according to the invention, the active element or elements other than copper are in a very particularly preferred manner selected from the alkali metals, alkaline-earth metals and rare earth metals.

In the catalyst according to the invention, the active elements are in a very particularly preferred manner copper, possibly magnesium, at least one alkali metal and possibly at least one rare earth metal.

In a truly very particularly preferred manner, the active elements are copper, magnesium, at least one alkali metal and possibly at least one rare earth metal.

Catalysts of which the active elements are copper, magnesium and at least one alkali metal yield good results.

Catalyst containing the following active elements yield very good results:

copper/magnesium/potassium, copper/magnesium/sodium; copper/magnesium/lithium, copper/magnesium/caesium, copper/magnesium/sodium/lithium, copper/magnesium/potassium/lithium and copper/magnesium/caesium/ lithium, copper/magnesium/sodium/potassium, copper/magnesium/sodium/caesium and copper/magnesium/potassium/caesium.

Catalysts containing the following active elements yield excellent results: copper/magnesium/potassium, copper/magnesium/sodium; copper/magnesium/lithium, copper/magnesium/caesium, copper/magnesium/sodium/lithium, copper/magnesium/potassium/lithium and copper/magnesium/caesium/lithium.

The copper content, calculated in metal form, is advantageously between 30 and 90 g/kg, preferably between 40 and 75 g/kg and in a particularly preferred manner between 50 and 70 g/kg of catalyst.

The magnesium content, calculated in metal form, is advantageously between 10 and 30 g/kg, preferably between 12 and 25 g/kg and in a particularly preferred manner between 15 and 20 g/kg of catalyst.

The alkali metal(s) content, calculated in metal form, is advantageously between 0.1 and 30 g/kg, preferably between 0.5 and 20 g/kg and in a particularly preferred manner between 1 and 15 g/kg of catalyst.

The Cu:Mg:alkali metal(s) atomic ratios are normally 1:0.1-2:0.05-2, preferably 1:0.2-1.5:0.1-1.5 and in a particularly preferred manner 1:0.5-1:0.15-1.

The catalyst according to the invention advantageously has a specific surface area measured by the BET method with nitrogen between 25 m$^2$/g and 300 m$^2$/g, preferably between 50 and 200 m$^2$/g and in a particularly preferred manner between 75 and 175 m$^2$/g.

The method for obtaining the catalyst according to the invention is not critical in itself. A preferred preparation method consists in impregnating an alumina according to the invention with an aqueous solution containing the desired quantities of salts of the active elements of the catalyst. Various additives including hydrochloric acid can be added to the aqueous solution. The impregnation can be carried out in one or more steps. It is preferably carried out in a single step. The impregnation is in a particularly preferred manner followed by a step of drying of the catalyst obtained.

The salts of the active elements used to impregnate the alumina can be oxides, hydroxides, nitrates, carbonates, acetates and chlorides. They are preferably chlorides.

The impregnation is advantageously carried out at a temperature above ambient temperature to favour the solubility of the impregnating salts.

The appearance of a liquid phase not adsorbed by the solid is advantageously avoided by limiting the volume of the impregnating solution to 70 to 100% of the pore volume of the quantity of alumina employed.

The invention further relates to the use of an alumina according to the invention as a support of the catalyst according to the invention.

For this purpose, the invention relates to the use of an alumina containing at least 0.03 g of titanium, expressed in metal form, per kg of alumina, as catalyst support.

The invention further relates to the use of an alumina according to the invention as a catalyst diluent. It can then be used as such, that is in unimpregnated form, or in a form impregnated with at least one active element.

For this purpose, the invention relates to the use of an alumina containing at least 0.03 g of titanium, expressed in metal form, per kg of alumina as catalyst diluent.

The catalyst according to the invention can be employed in any method involving a gas phase reaction.

This is why the invention further relates to a method involving a gas phase reaction in which the gas phase reaction is catalysed by the catalyst according to the invention.

The gas phase reaction is preferably an oxidation reaction of a hydrocarbon, in a particularly preferred manner an oxychlorination reaction of a hydrocarbon containing 1 to 4 carbon atoms.

The hydrocarbons containing 1 to 4 carbon atoms include methane, ethane, ethylene, propane, propylene, butenes, acetylene, chloroethane, chloropropane, dichloromethane and dichloroethane.

In a very particularly preferred manner, the gas phase reaction is the oxychlorination reaction of ethylene to 1,2-dichloroethane.

The oxychlorination reaction can take place in a fixed bed or a fluidized bed.

If the reaction takes place in a fixed bed, the catalyst according to the invention is preferably in the form of granules or pellets of any shape. If the reaction takes place in a fluidized bed, the catalyst according to the invention is preferably in powder form.

The oxychlorination reaction preferably takes place in a fluidized bed.

The molecular oxygen necessary for the oxychlorination reaction is advantageously introduced into the reactor, either diluted, for example in the form of air, or pure. The oxygen is preferably introduced pure into the reactor.

The temperature at which the oxychlorination reaction takes place is normally between 200 and 300° C., preferably between 220 and 280° C., in a particularly preferred manner between 230 and 270° C.

The pressure at which the oxychlorination reaction takes place is not critical in itself. Normally, it takes place at pressures between 0.1 and 1 MPa and preferably between 0.1 and 0.8 MPa.

The fluidizing rate of the catalyst according to the invention during the oxychlorination reaction is not critical in itself Its choice essentially depends of the particle size distribution of the catalyst and the dimensions of the apparatus. In general, the operation takes place with fluidizing rates between 5 and 100 cm/s.

Finally, the ratio of the reactants employed for the oxychlorination reaction is the same as the one generally used in prior methods. Normally, the operation takes place with a slight excess of ethylene with respect to the stoichiometric quantity necessary to react with the HCl employed However, the catalyst according to the invention serves equally to operate with large excesses of ethylene or in the neighbourhood of stoichiometry, or indeed even with an excess of HCl.

The catalyst according to the invention not only presents the advantage of procuring, for the method in which it is used, a stable oxygen profile in the tail gases and hence in the recycled gases, but also of ensuring a stable ethylene content in these gases. This is an economic advantage because the ratio of hydrogen chloride to total ethylene (recycling included) sent to the reactor is a primary parameter for the effective control of an oxychlorination reaction: it conditions the conversion yield An uncontrolled excess can raise various problems such as corrosion and caking in the case of the fluidized bed. It is also evident that a continuous variation, to be offset in real time, represents a greater workload, avoided in the case of the present invention.

The following examples are intended to illustrate the invention without limiting its scope.

EXAMPLE 1

According to the Invention

A catalyst was initially prepared from a hydrated alumina of the PURAL SCC 30 type marketed by SASOL (ex-CONDEA Chemie GmbH) which was calcined to obtain an alumina with a specific surface area of 180 m²/g. This alumina contained 1.13 g of titanium expressed in metal form, per kg of alumina. The titanium content was measured by inductively coupled plasma optic emission spectrometry (ICP-OES) after complete dissolution of the sample. This alumina exhibited the following other properties: pore volume=0.35 cm³/g; bulk density (measured by free flow) 0.7 kg/dm³, and mean particle diameter=47 μm.

To about 750 g of this alumina, an aqueous impregnation solution was added comprising, in the dissolved state, 162 g of $CuCl_2.2H_2O$, 144 g of $MgCl_2.6H_2O$, 17.2 g of KCl and 10.6 g of LiCl. The wet solid was then heated at 180° C. for 18 h. 1 kg of catalyst was thus obtained with, calculated in metal form with respect to the total weight of catalyst, a copper content of 60 g/kg, a magnesium content of 17 g/kg, a potassium content of 9 g/kg and a lithium content of 1.75 g/kg. Expressed as an atomic ratio, the proportion of the various metals Cu:Mg:K:Li was 1:0.74:0.24:0.26.

EXAMPLE 2

According to the Invention

About 16 tons of catalyst prepared by the method described in Example 1 were placed in an industrial fluidized bed reactor for the oxychlorination of ethylene to 1,2-dichloroethane.

In this reactor, the gases were introduced from the bottom through a gas distribution device. The operating conditions in which Example 2 was carried out are as follows:
reactant throughput (t/h): $C_2H_4/HCl/O_2$: 2.7/7.5/1.9
temperature: 246° C.
pressure: 0.49 MPa
fluidizing rate: 33 cm/s
contact time: 26 s.

The operating parameters of the oxychlorination reaction were observed for 24 hours and are shown in FIG. 1, which shows the variation in the oxygen (plot A) content (% by volume) and the ethylene (plot B) content (% by volume) in the tail gases during the 24 hour period (the x-axis shows the time in hh.mm). It may be observed that the oxygen and ethylene contents of the tail gases have remained reasonably constant over time.

EXAMPLE 3

Comparative

A catalyst was prepared following the same procedure as in Example 1 starting with a hydrated alumina of the PURAL SCC 30 marketed by SASOL (ex-CONDEA Chemie GmbH), which was calcined to obtain an alumina with a specific surface area of 180 m²/g. Unlike the alumina in Example 1, the alumina concerned in Example 3 contained 0.015 g of titanium, expressed in metal form, per kg of alumina The titanium content was also measured by inductively coupled plasma optic emission spectrometry (ICP-OES) after complete dissolution of the sample. This alumina exhibited the following properties: pore volume=0.35 cm³/g; bulk density (measured by free flow) 0.70 kg/dm³ and mean particle diameter=46 μm.

EXAMPLE 4

Comparative

About 16 tons of catalyst prepared by the method described in Example 3 were placed in the same reactor as the one described in Example 2.

In this reactor, the gases were introduced from the bottom through a gas distribution device. The operating conditions in which the Example 4 was carried out are as follows:
reactant throughput (t/h): $C_2H_4/HCl/O_2$: 3/8.5/2.1
temperature: 250° C.
pressure: 0.52 MPa
fluidizing rate: 33 cm/s
contact time: 26 s.

Figure 2:
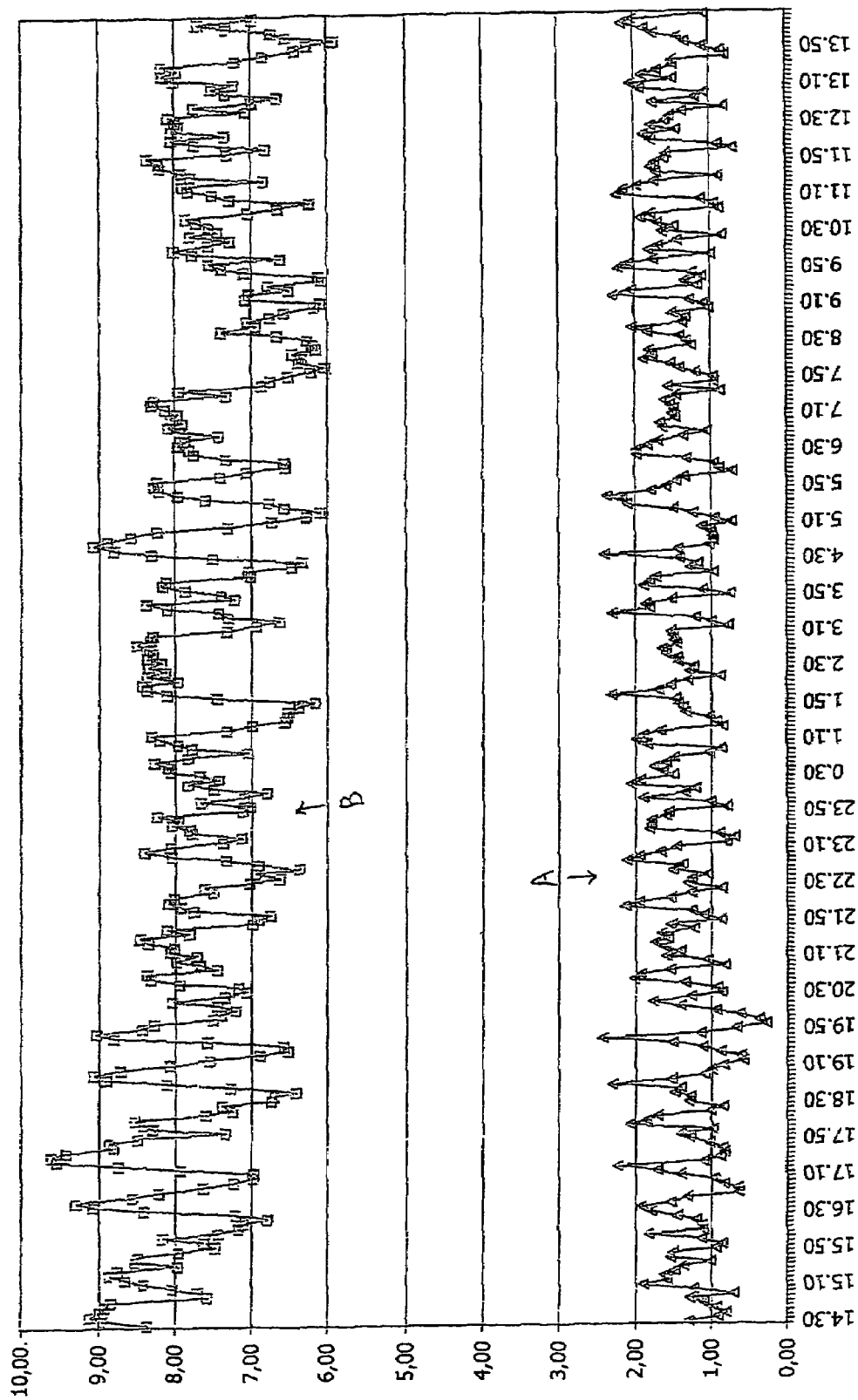

The operating parameters of the oxychlorination reaction were observed for 24 hours and are shown in FIG. 2, which shows the variation in the oxygen (plot A) content (% by volume) and the ethylene (plot B) content (% by volume) in the tail gases during the 24 hour period (the x-axis shows the time in hh.mm). The variation in the oxygen content of the tail gases was impressive. It went steadily and rapidly from less than 0.8 to over 2% by volume and vice versa, requiring the operator to make incessant corrections to prevent the unit from being stopped by the safety automation. The ethylene content of the tail gases also showed rapid sudden variations between 6-7% by volume and over 9% by volume.

EXAMPLE 5

According to the Invention

About 16 tons of catalyst prepared by the method described in Example 1 were placed in an industrial fluidized bed reactor for the oxychlorination of ethylene to 1,2-dichloroethane.

In this reactor, the gases were introduced from the bottom through a gas distribution device. The operating conditions in which Example 5 was carried out are as follows:
reactant throughput (t/h): $C_2/HCl/O_2$: 3.1/8.6/2.2.
temperature: 246.4° C.
pressure: 0.52 MPa
fluidizing rate: 33 cm/s
contact time: 26 s.

Figure 3:
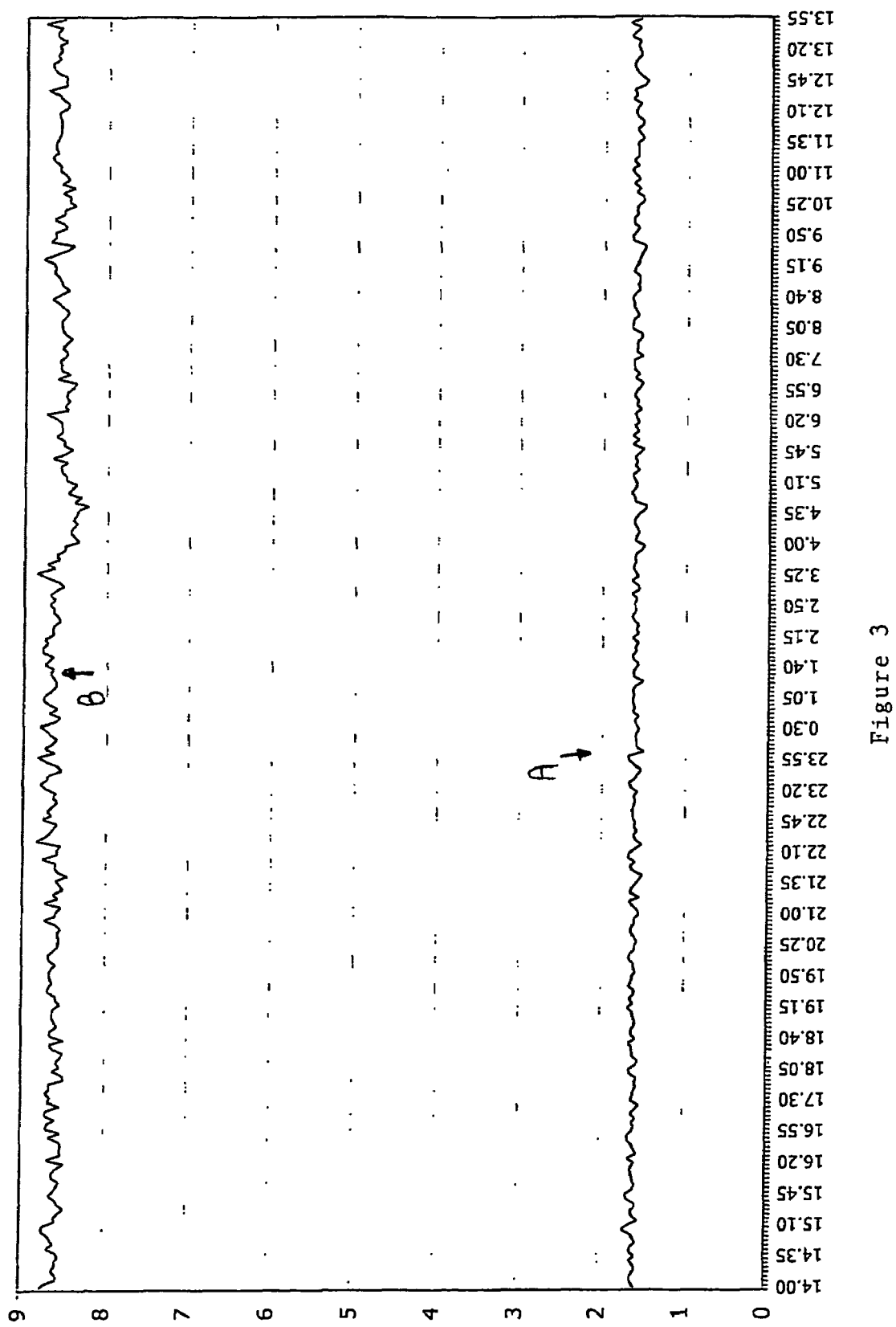

The operating parameters of the oxychlorination reaction were observed for 24 hours and are shown in FIG. 3, which shows the variation in the oxygen (plot A) content (% by volume) and the ethylene (plot B) content (% by volume) in the tail gases during the 24 hour period (the x-axis shows the time in hh.mm). It may be observed that the oxygen and ethylene contents of the tail gases have remained reasonably constant over tome.

The invention claimed is:

1. A catalyst comprising copper and at least one other active element deposited on an alumina support, said alumina support comprising at least 0.03 g of titanium therein, expressed in metal form, per kg of alumina.

2. The catalyst according to claim 1, wherein the alumina support comprises at most 15 g of titanium therein, expressed in metal form, per kg of alumina.

3. The catalyst according to claim 1, wherein the alumina support comprises at least 0.05 g of titanium therein, expressed in metal form, per kg of alumina.

4. The catalyst according to claim 1, wherein the alumina support comprises at most 5 g of titanium therein, expressed in metal form, per kg of alumina.

5. The catalyst according to claim 1 wherein the at least one other active element deposited on said alumina support is selected from the group consisting of alkali metals, alkaline-earth metals, rare earth metals and metals of the group consisting of ruthenium, rhodium, palladium, osmium, iridium, platinum and gold.

6. The catalyst according to claim 1, wherein the at least one other active element deposited on said alumina support is selected from the group consisting of alkali metals, alkaline-earth metals and rare earth metals.

7. The catalyst according to claim 1, comprising, in addition to copper, magnesium and at least one alkali metal deposited on said alumina support.

8. The catalyst according to claim 1, wherein the alumina support comprises at least 0.2 g of titanium therein, expressed in metal form, per kg of alumina.

9. The catalyst according to claim 1, wherein the alumina support comprises at most 1.5 g of titanium therein, expressed in metal form, per kg of alumina.

10. The catalyst according to claim 1, wherein said alumina support comprises at least 0.05 g and at most 5 g of titanium therein, expressed in metal form, per kg of alumina, and wherein the catalyst comprises between 30 and 90 g of copper, calculated in metal form, per kg of catalyst.

11. The catalyst according to claim 1, wherein said alumina support comprises at least 0.03 g and at most 15 g of titanium therein, expressed in metal form, per kg of alumina, and wherein the catalyst comprises between 30 and 90 g of copper, calculated in metal form, per kg of catalyst.

12. In a gas phase reaction, the improvement wherein the gas phase reaction is catalyzed by a catalyst according to claim 1.

13. The gas phase reaction according to claim 12, wherein the gas phase reaction is an oxidation reaction of a hydrocarbon.

14. The gas phase reaction according to claim 12, wherein the gas phase reaction is an oxychlorination reaction of a hydrocarbon containing 1 to 4 carbon atoms.

15. The gas phase reaction according to claim 12, wherein the gas phase reaction is the oxychlorination reaction of ethylene to 1,2-dichloroethane.

16. A catalyst support or diluent consisting of alumina comprising at least 0.03 g of titanium therein, expressed in metal form, per kg of alumina.

17. The catalyst support according to claim 16, wherein said alumina comprises at least 0.03 g and at most 15 g of titanium therein, expressed in metal form, per kg of alumina.

18. The catalyst support according to claim 16, wherein said alumina comprises at least 0.05 g and at most 5 g of titanium therein, expressed in metal form, per kg of alumina.

19. The catalyst support according to claim 16, wherein said alumina comprises at least 0.2 g and at most 1.5 g of titanium therein, expressed in metal form, per kg of alumina.

* * * * *

UNITED STATES PATENT AND TRADEMARK OFFICE
CERTIFICATE OF CORRECTION

PATENT NO. : 7,612,244 B2  Page 1 of 1
APPLICATION NO. : 10/579094
DATED : November 3, 2009
INVENTOR(S) : Strebelle et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 555 days.

Signed and Sealed this

Nineteenth Day of October, 2010

David J. Kappos
*Director of the United States Patent and Trademark Office*